United States Patent
Ibrahim

(10) Patent No.: US 7,260,435 B2
(45) Date of Patent: Aug. 21, 2007

(54) TRANSCEIVER COIL FOR AUDITORY PROSTHESIS

(75) Inventor: Ibrahim Hanna Ibrahim, North Ryde (AU)

(73) Assignee: Cochlear Limited, Lane Cove, New South Wales (AU)

( * ) Notice: Subject to any disclaimer, the term of this patent is extended or adjusted under 35 U.S.C. 154(b) by 519 days.

(21) Appl. No.: 10/250,831

(22) PCT Filed: May 22, 2002

(86) PCT No.: PCT/AU02/00640

§ 371 (c)(1),
(2), (4) Date: Jul. 7, 2003

(87) PCT Pub. No.: WO02/094370

PCT Pub. Date: Nov. 28, 2002

(65) Prior Publication Data
US 2004/0044382 A1 Mar. 4, 2004

(30) Foreign Application Priority Data
May 23, 2001 (AU) .................. PR5203

(51) Int. Cl.
A61N 1/00 (2006.01)
(52) U.S. Cl. .......................... 607/57; 607/60
(58) Field of Classification Search ............ 607/32, 607/60, 55–57; 128/903, 904; 600/300; 604/891.1; 455/851
See application file for complete search history.

(56) References Cited

U.S. PATENT DOCUMENTS

| 4,532,930 | A |  | 8/1985 | Crosby et al. |
| 4,654,880 | A |  | 3/1987 | Sontag |
| 5,656,849 | A |  | 8/1997 | Burghartz et al. |
| 5,781,077 | A |  | 7/1998 | Leitch et al. |
| 5,898,403 | A |  | 4/1999 | Saitoh et al. |
| 5,967,989 | A | * | 10/1999 | Cimochowski et al. ..... 600/459 |
| 5,991,664 | A |  | 11/1999 | Seligman |
| 6,738,650 | B1 | * | 5/2004 | Zhou et al. ............ 455/575.5 |

FOREIGN PATENT DOCUMENTS

| EP | 0 932 255 A2 | 7/1999 |
| GB | 2 333 062 A | 7/1999 |
| WO | WO 98/29881 | 7/1998 |
| WO | WO 99/42176 | 8/1999 |

(Continued)

OTHER PUBLICATIONS

International Search Report of PCT/AU02/00640, dated Aug. 6, 2002.

(Continued)

Primary Examiner—Mark Bockelman
(74) Attorney, Agent, or Firm—Christie, Parker & Hale, LLP

(57) ABSTRACT

The invention provides a tuned transmitter coil for transcutaneous transmission of power and information from an external component of an auditory prosthesis to an implanted receiver. A shield is provided in order to reduce a skin-to-coil capacitance, thereby improving tuning stability of the coil from one user to the next. A shield may also be provided in order to reduce electromagnetic interference.

82 Claims, 7 Drawing Sheets

FOREIGN PATENT DOCUMENTS

WO    WO 00/02212    1/2000

OTHER PUBLICATIONS

International Preliminary Examination Report of PCT/AU02/00640, dated Dec. 10, 2002.

Chen, et al., "Q-Enhancement of Spiral Inductor with $N^+$-Diffusion Patterned Ground Shields" 2001 IEEE MTT-S Digest, pp. 1289-1292, Atlanta, GA, USA.

Supplementary Partial European Search Report for related European Patent Application EP 02 72 9626 mailed Dec. 1, 2006.

* cited by examiner

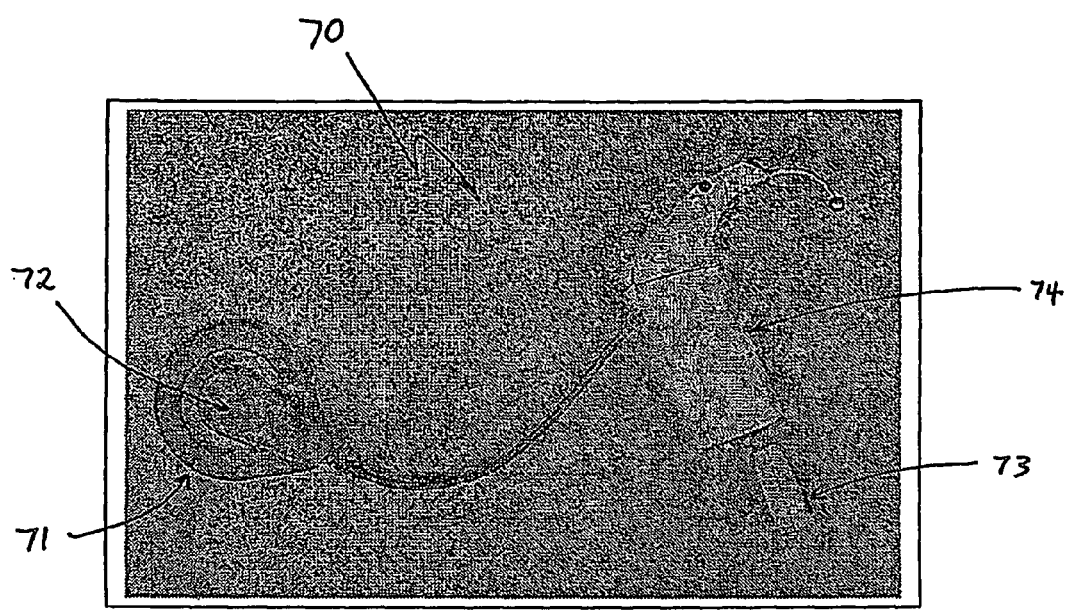
Figure 7
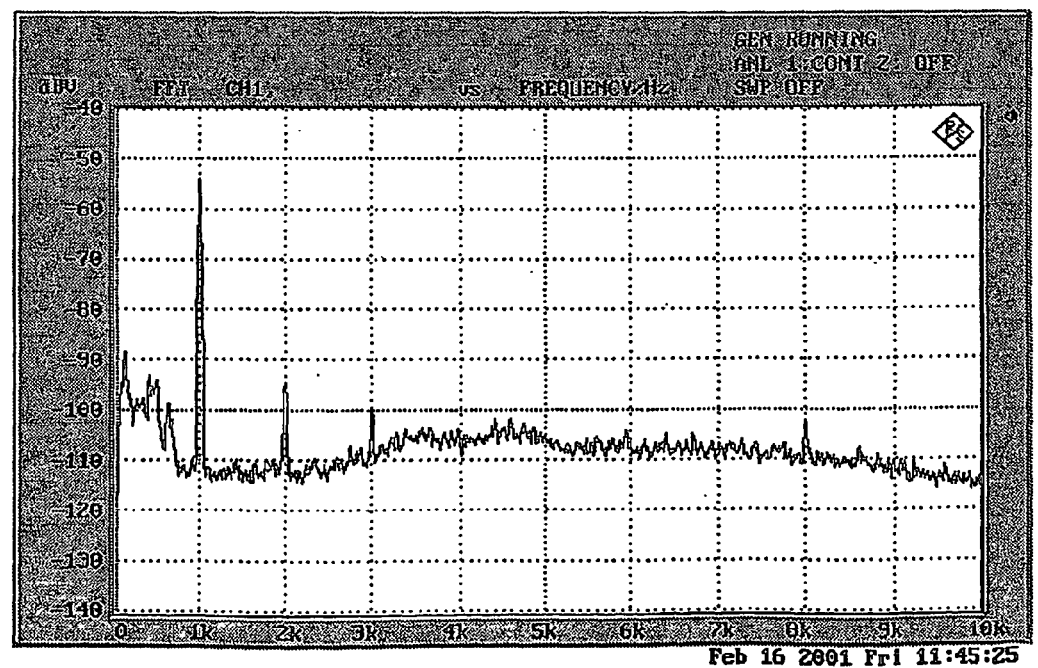
Figur 8

TRANSCEIVER COIL FOR AUDITORY PROSTHESIS

CROSS-REFERENCE TO RELATED APPLICATION

This application is a National Phase Patent Application of International Application Number PCT/AU02/00640, filed on May 22, 2002, which claims priority of Australian Patent Application Number PR 5203, filed May 23, 2001.

TECHNICAL FIELD

The present invention relates to a transceiver coil for an auditory prosthesis, and to a system comprising such a transceiver coil. In particular, the present invention relates to a high performance PCB coil for forming a transcutaneous link in an auditory prosthesis.

BACKGROUND ART

In many people who are profoundly deaf, the reason for deafness is absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil tuned to a desired frequency of transmission.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of an RF link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

As previously mentioned, the most commonly accepted method of providing the implanted stimulator with power and information is to transmit RF-power via an inductively coupled coil system. In such a system, the external transmitter coil is usually positioned on the side of the users head directly facing the coil of the stimulator/receiver unit to allow for the transmission of the coded sound signal and power from the speech processor to the implanted stimulator unit. In this way the transmitter and receiver coils form a transformer allowing for the transfer of energy from the external processor unit to the implanted stimulator/receiver unit. Such transmitters usually have a coil formed by a small number of turns of a single or multi-strand wire, and a magnet at the hub of the coil. The magnet holds the transmitter coil in place due to magnetic attraction with the implant. The diameters of each coil are typically between 15 and 30 mm.

The geometric characteristics of the coils are usually set to ensure high power transfer efficiency, which is often determined by the distance between the coils. Often, to achieve a high amount of inductive coupling, the distance between the coils must be sufficiently small compared to the diameter of the coils, with a high amount of inductive coupling ensuring high power transfer efficiency. It is known to use tuned or tank circuits in the transmitter and receiver coils to transmit the power and data, as is disclosed in U.S. Pat. No. 4,654,880.

The present invention therefore provides an improved transmission device for use in transcutaneous communication of medical devices that overcomes a number of the problems intrinsic to earlier devices.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention resides in a tuned transmitter coil for transcutaneous RF transmission of power and information from an external component of an auditory prosthesis to an implanted receiver, the transmitter coil comprising a first shield for reducing a skin-to-coil capacitance.

According to a second aspect, the present invention provides a transceiver for an auditory prosthesis, the transceiver comprising:

a tuned transmission coil for transcutaneous transmissions, tuned to a desired frequency of transmission; and a first shield for reducing a skin-to-coil capacitance.

According to a third aspect the present invention provides an external processor unit for an auditory prosthesis, the external processor unit comprising:

a transceiver comprising a tuned transmission coil for transcutaneous transmission, tuned to a desired frequency of transmission; and a first shield for reducing a skin-to-coil capacitance.

It has been realised that in order to increase efficiency of transmission, it is desirable to tune a transmission coil by use of a relatively large inductance and a relatively small capacitance. However, when a small capacitance is used to tune the coil, the presence of stray capacitance such as the skin-to-coil capacitance, can have a considerable impact on tuning frequency. It has further been realised that a skin-to-coil capacitance can vary considerably from one user to the next, for example due to differing skin thickness proximal to the coil, making it difficult to compensate for such capacitance when designing a coil. By providing a shield for reducing a skin-to-coil capacitance, the present invention improves the stability of a tuned frequency of the coil when brought close to a user's skin.

Furthermore, in a transcutaneous wireless link the critical parameter for power transmission is the coupling coefficient between the external tuned coil and the internal tuned coil. The coupling coefficient is optimal only at a critical spacing between the coils, and for optimal coupling the two coils must be spaced at the critical distance from each other and must be co-axial. If this is not the case then the exchange between both components is at a reduced efficiency. Therefore, it has been realised that it is important that the coils forming the transcutaneous link are designed in such a way as to optimise the transfer of power and data from the external processor to the implanted stimulator/receiver.

This aspect is further complicated by the fact that, due to variations in the anatomical characteristics of each implantee, the inter-coil distance is not constant from patient to patient. Further, it has been realised that, as human tissue has low conductivity, the tuned frequency of such coils has in the past been sensitive to characteristics of skin when in close proximity to the skin.

The first shield for reducing the skin-to-coil capacitance is preferably integrally formed with the transmission coil, and positioned relative to the coil so as to be positioned between the coil and a user's skin when the transceiver is placed against the user's skin.

The transmission coil is preferably implemented by use of printed circuit board (PCB) technology. In such embodiments, the transmission coil preferably comprises first and second adjacent PCB layers, each layer having a track defining a generally circular spiral with a plurality of turns.

The characteristics of the transmission coil can be controlled or selected in order to optimise performance of the coil. For instance, characteristics of the transmission coil such as dimensions of the track, the number of turns of each spiral, the radial spacing of each turn of the spirals, the substrate material and dimensions, the track material, the position of the spiral of the first layer relative to the spiral of the second layer, and other such characteristics of the transmission coil, may be selected or controlled in order to define electrical characteristics of the transmission coil such as transmission coil quality factor (Q-factor), transmission coil inductance, transmission coil self-capacitance, and the sensitivity of the tuning frequency to stray capacitances. For instance, each turn of the spiral of the first layer is preferably placed adjacent to a gap between turns of the spiral of the second layer, rather than being placed adjacent to a turn of the spiral of the second layer. Such placement reduces the capacitance between the first and second layers, and hence reduces the self-capacitance of the transmission coil.

In such embodiments, the transmission coil preferably further comprises a third PCB layer integrally formed with the first and second PCB layers, on which the first shield is formed. The first shield is preferably defined by tracks of the third layer, and the first shield preferably extends in a region generally adjacent to the spirals of the first and second layers. The tracks defining the first shield are preferably in the form of a plurality of generally concentric open loops, with each of the open loops preferably being electrically grounded.

Characteristics of the first shield are preferably selected or controlled in order to optimise shielding while avoiding large shield-to-coil capacitance. For instance, the tracks defining the open loops of the first shield preferably have a small width relative to a width of the tracks of the first and second layers. Further, each open loop of the first shield is preferably placed adjacent to a gap between turns of the spiral of the adjacent layer, rather than being placed adjacent to a turn of the spiral of the adjacent layer. Such placement reduces the capacitance between the first shield and the transmission coil.

The transmission coil preferably further comprises a second shield for reducing electromagnetic emissions from the transmission coil. In many environments, electromagnetic emissions of a transmission coil of an auditory prosthesis have the potential to interfere with electronic equipment. For example, in hospital or clinical environments a user of such a prosthesis may be required to turn the prosthesis off to ensure the electromagnetic emissions of the coil do not interfere with critical electronic systems. However, effective shielding enables the use of the transmission coil in closer proximity to electrical equipment without exceeding allowable levels of emissions, thereby reducing the interference.

The second shield is preferably placed on a side of the transmission coil opposite to the side of the transmission coil on which the first shield is placed. In embodiments where the transmission coil is implemented using PCB technology, the second shield is preferably defined by tracks on a fourth layer of the transmission coil. The second shield preferably extends in a region generally adjacent to the spirals of the first and second layers. The tracks defining the second shield are preferably in the form of a plurality of generally concentric open loops, with each of the open loops preferably being electrically grounded.

Characteristics of the second shield are preferably selected or controlled in order to optimise shielding while avoiding large shield-to-coil capacitance. For instance, the tracks defining the open loops of the second shield preferably have a small width relative to a width of the tracks of the first and second layers. Further, each open loop of the second shield is preferably placed adjacent to a gap between turns of the spiral of the adjacent layer, rather than being placed adjacent to a turn of the spiral of the adjacent layer. Such placement reduces the capacitance between the second shield and the transmission coil.

According to a fourth aspect, the present invention provides an external processor unit for an auditory prosthesis, the external processor unit comprising:

a transmission coil for transmission of transcutaneous electromagnetic signals to an implant;

a receiver for receiving wireless transmissions from a signal source; and a shield for reducing electromagnetic emissions of the transmission coil.

In many environments, particularly teaching environments, a FM receiver is used in conjunction with an auditory prosthesis in order to improve signal quality received by the prosthesis. However, the use of a wireless transcutaneous link by the auditory prosthesis has, in the past, generated significant electromagnetic interference (EMI). Such EMI can interfere with FM reception, which has necessitated placement of the FM receiver a significant distance from the auditory prosthesis, which can be inconvenient for a user of the auditory prosthesis. Accordingly, it has been realised that there is a need to minimise the amount of electromagnetic radiation emitted by the coil.

The external processor unit may be adapted for mounting on a user's ear, or may be adapted for mounting on a user's belt. Alternately the external processor unit may reside in a user's pocket. The external processor unit preferably includes a cable to the transmission coil to allow the transmission coil to be placed behind a user's ear, for coupling with an implant.

By shielding electromagnetic emissions of the transmission coil, the present invention allows an FM receiver to be placed much closer to the transmission coil, and in particular allows the FM receiver to become a part of the external processor unit of the auditory prosthesis, even when the external processor unit is mounted on a users ear, within centimetres of the transmission coil. Further, some embodiments of the present invention may provide sufficient shielding to satisfy electromagnetic compatibility (EMC) standards, enabling use of such an auditory prosthesis in environments which are sensitive to EMI and which require compliance with such standards.

The transceiver is preferably operable to transmit RF power and RF modulated information to an implanted portion of the auditory prosthesis. The transceiver is preferably also operable to receive RF signals from the implanted portion of the auditory prosthesis, for example signals relating to an operating status of the implanted portion or signals relating to physiological characteristics measured by the implanted portion.

According to a fifth aspect the present invention provides an antenna for subcutaneous communication comprising at least one turn of a wire, the at least one turn being housed in a casing, wherein the casing comprises:

a cable inlet for accommodating a cable connection to the at least one turn;

an outer portion housing the at least one turn, wherein distal from the cable inlet the outer portion defines a substantially semicircular annulus following a nominal circumference of a nominal circle, wherein the cable inlet is positioned outside the nominal circumference, and wherein proximal to the cable inlet the outer portion extends substantially tangentially to the nominal circumference towards the cable inlet; and an inner portion for housing magnetic means, the inner portion being connected to the outer portion proximal to the cable inlet, wherein the inner portion extends inside the nominal circle formed by the outer portion so as to position the magnetic means substantially at a centre of the nominal circle.

The inner portion may be integrally formed with the outer portion, and the casing may be formed of plastic. The outer portion may be a substantially rectangular cross-section annulus, so as to accommodate embodiments in which the at least one turn is formed on a printed circuit board.

Embodiments of the fifth aspect of the invention may be advantageous in that only a single "spoken" is provided in supporting the magnetic means, thus reducing materials and weight required in forming the antenna casing as compared to the required materials and weight of a "hub and spoke" antenna design. Further, the fifth aspect of the present invention may be advantageous in facilitating automated production of antennae in which the at least one turn of the antenna is formed on a PCB. In particular, having a single spoke simplifies the shape of a casing and increases the ease of construction of a 2-part "snap-fit" mould into which such a PCB is to be placed, as a reduced number of spokes are present requiring the snap fit. The fifth aspect of the invention may also provide a stylised attractive antenna, which can be an important consideration where the antenna is to be worn by a user in a prominent body position, such as on the head behind the ear.

BRIEF DESCRIPTION OF DRAWINGS

By way of example only, preferred embodiments of the invention are described with reference to the accompanying drawings, in which:

FIG. 9b is a front view of the antenna of FIG. 9a;

DESCRIPTION OF THE INVENTION

Figure 1A:
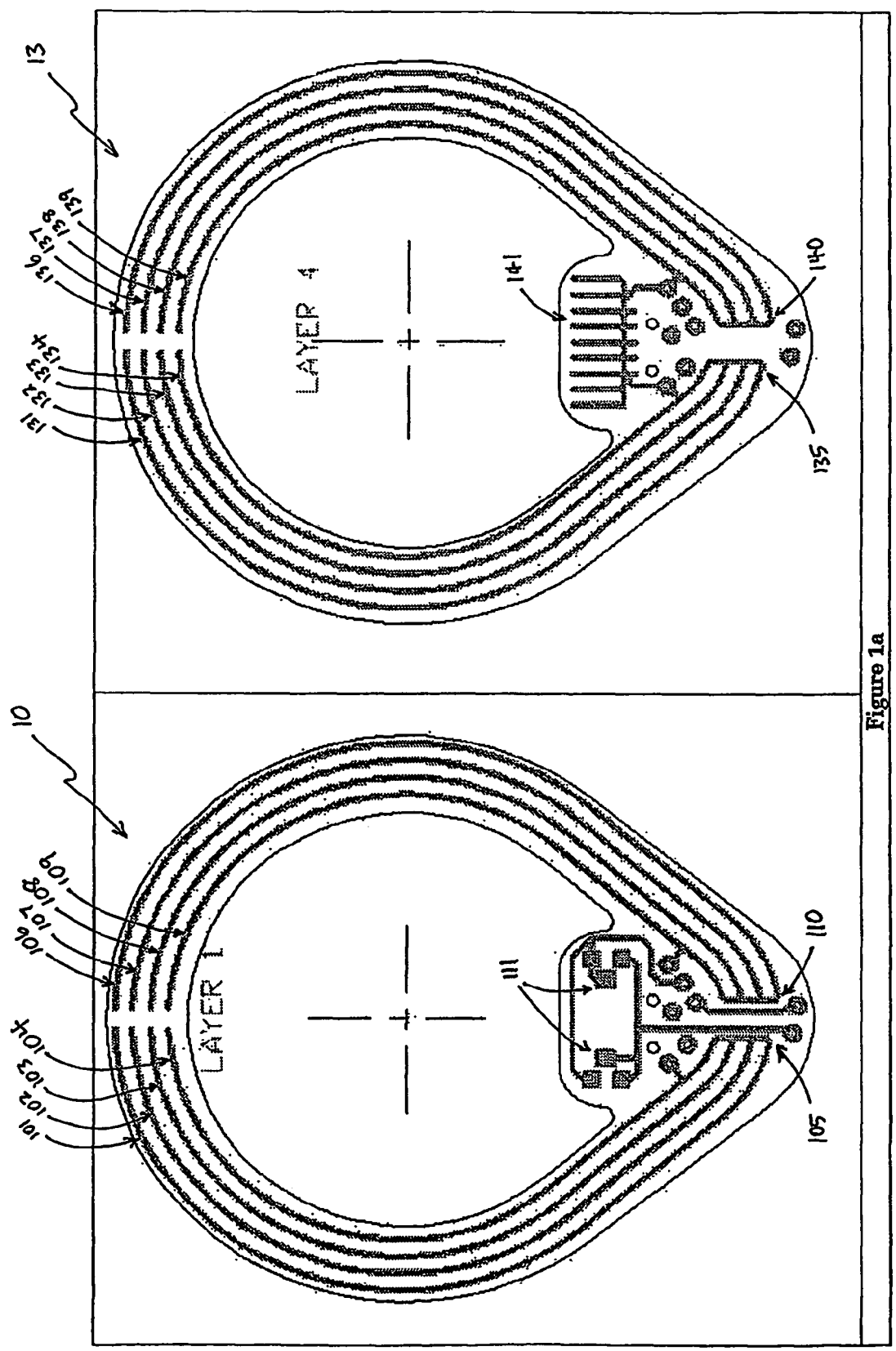
FIGS. 1a and 1b illustrate the layers of a transceiver in accordance with the present invention.
Figure 1B:
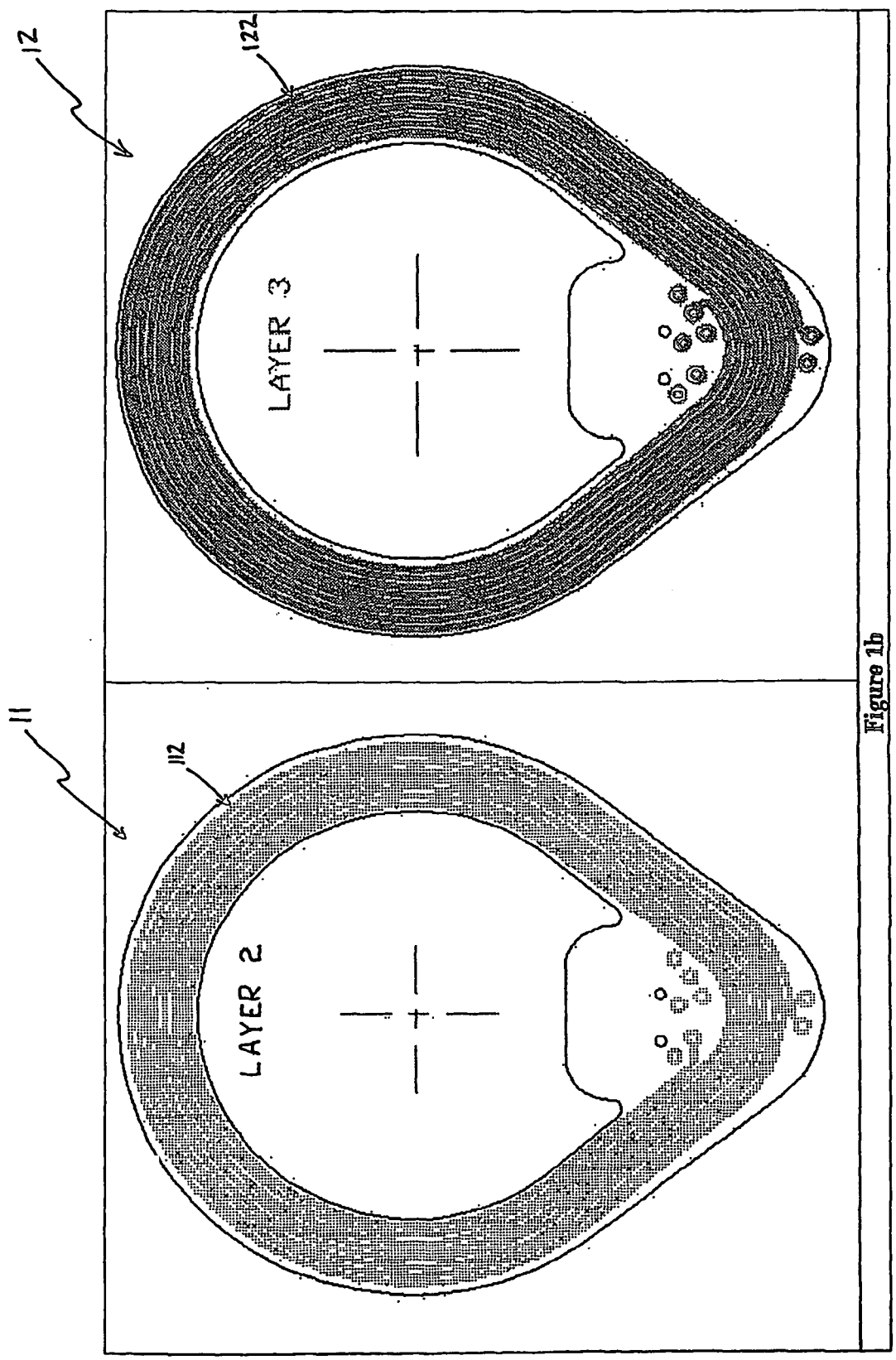

FIGS. 1a and 1b illustrate the layers of a transceiver for an auditory prosthesis in accordance with the present invention. The embodiment shown is based on standard PCB technology, although it will be appreciated that the present invention may be implemented otherwise. A low dielectric constant PCB material is used to reduce the shield-to-coil capacitance as well as the self-capacitance of the coil. A four layer PCB is used, where the top and bottom layers 10 and 13 are used for electrostatic shielding, and are electrically insulated from the transmission coil. The two inner layers 11 and 12 are used for the transmission inductor. FIGS. 1a and 1b depict the design of the different layers of a 16-turn coil.

The PCB material, layer thicknesses, copper track width and spacing are optimised to achieve maximum tuning frequency stability. This is to minimise the drift in tuning frequency due to varying stray capacitance, and also due to changes in temperature and humidity.

The top shield layer 10 shown in FIG. 1a comprises tracks defining four open loops 101, 102, 103, 104 shorted together at 105, and further comprises four open loops 106, 107, 108 and 109 shorted together at 110. Similarly, shield layer 13 also comprises tracks defining four open loops 131, 132, 133, 134 shorted together at 135, and further comprises four open loops 136, 137, 138 and 139, shorted together at 140. For both shield layers 10 and 13, the width, spacing and positioning of the tracks are optimised for good electrostatic shielding to the transmission coil and tuning capacitors without introducing large coil-to-shield capacitance. In the present embodiment, the total distributed shield-to-coil capacitance is about 20 pF.

Shield layer 10 also includes solder pads 111 for tuning capacitors, to allow tuning of the transmission coil to a desired transmission frequency. The bottom shield layer 13 has tracks defining a hashed area 141 under the tuning capacitors to provide electrostatic shielding to those capacitors. The two shield layers 10 and 13 are connected together and are grounded.

The inductor layers 11 and 12 form a transmission coil for transmission of power and information between an external processing unit and an implanted portion of an auditory prosthesis. As can be seen, the transmission coil comprises first and second adjacent PCB layers 11 and 12, the layers 11 and 12 having respective tracks 112 and 122 each defining a generally circular spiral with eight turns. The spirals of the first and second layers are both wound clockwise, from an inner portion of the spiral.

Figure 3:
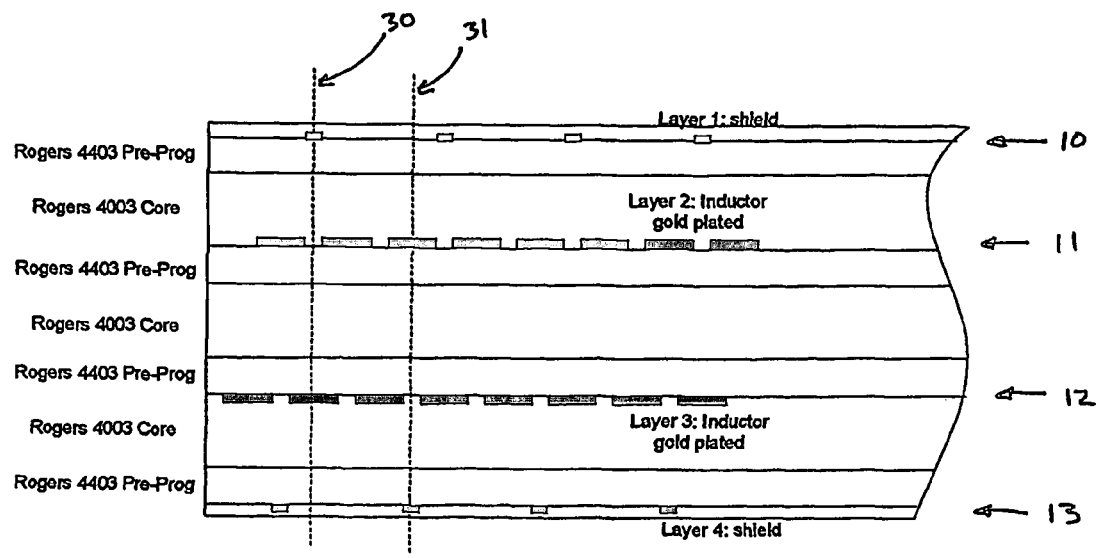
FIG. 3 is a partial cross-sectional view illustrating the relative positioning of the layers of the transceiver of FIG. 1.

The width and pitch of the tracks 112 and 122 are chosen to achieve maximum quality factor of the transmission coil at the smallest possible self-capacitance. The self-capacitance of the transmission coil is reduced by having the coil tracks on each layer overlaying the spaces between the tracks on the other layer, as shown in FIG. 3 and discussed in more detail in the following. This reduces the direct copper-to-copper area and reduces the self-capacitance of the coil. The quality factor is also improved by gold plating the copper tracks of the inductor layers 11 and 12.

The coil dimensions and number of turns are chosen to achieve the required inductance, and the required coupling coefficient between the transmitter and receiver coils.

In the present embodiment, the inductance of the transmitter coil is about 15 µH. The coupling coefficient between the transmitter coil and a 32 mm diameter sub-cutaneous receiver coil is higher than 10% at 10 mm spacing between the coils.

Figure 2:
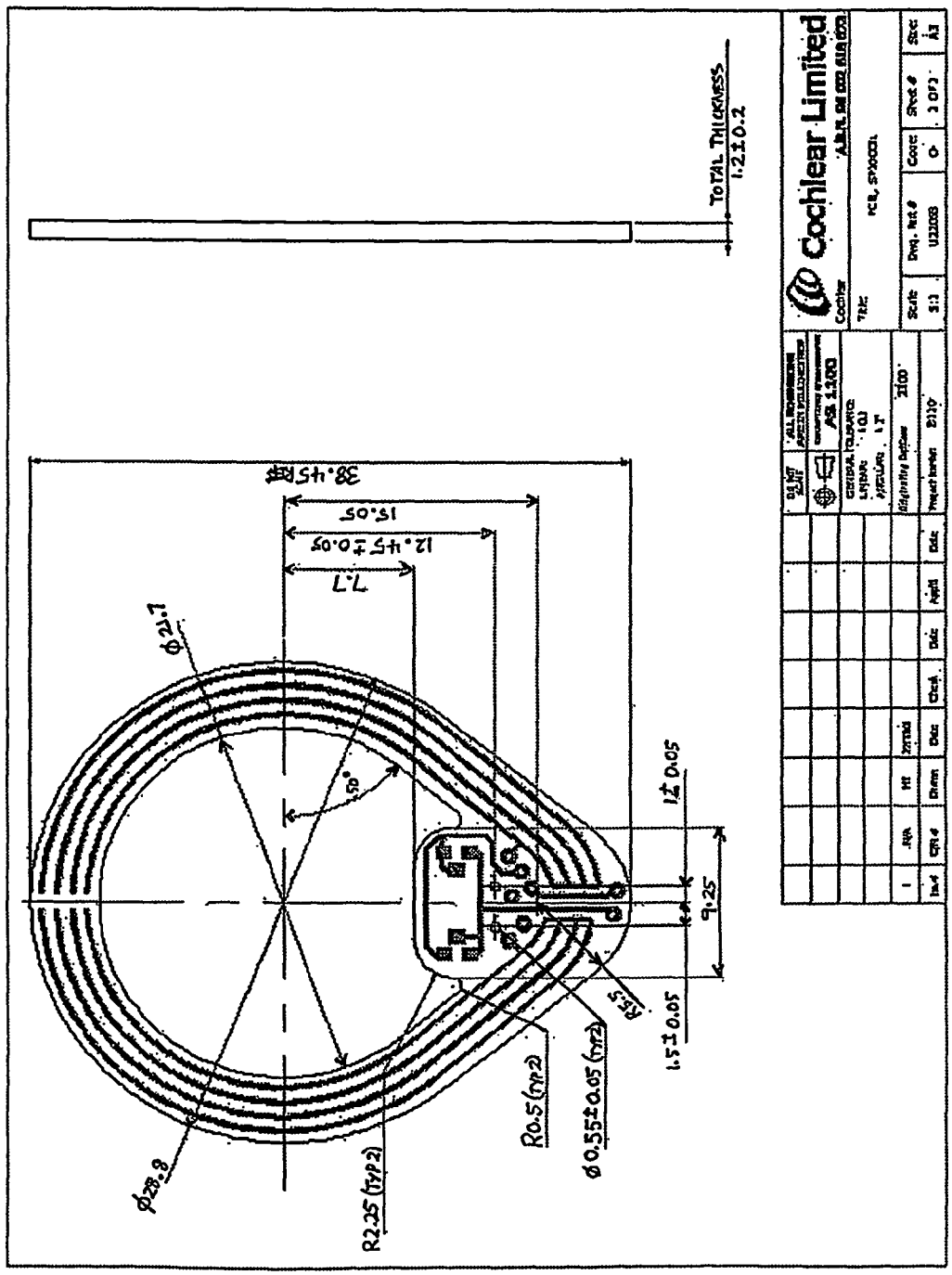
FIG. 2 illustrates physical dimensions of the transceiver of FIG. 1.

The dimensions of the coil in the present embodiment are shown in FIG. 2. The printed circuit board material used in the present embodiment is Rogers 4003. The FR4 material, Flex PCB or any other suitable PCB material could also be used if slightly higher shield-to-coil capacitance and self-capacitance are allowed.

FIG. 3 is a partial cross-sectional view illustrating the transmission coil and shields as formed in a multi-layer PCB. As can be seen, the tracks of layers 10, 11, 12 and 13 are interlaced, in order to reduce the shield-to-coil capacitance and the coil self-capacitance. That is, each track of the shield layer 10 is positioned adjacent to a gap between the tracks of adjacent layer 11, as indicated at 30. Similarly, each track of the coil layer 11 is situated adjacent to a gap between turns of the spiral of layer 12, as indicated at 31. The tracks of layers 12 and 13 are similarly interlaced.

Figure 4:
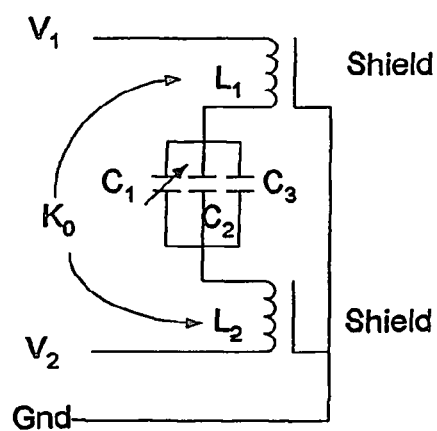
FIG. 4 is a schematic representation of the transceiver of FIG. 1.

FIG. 4 shows a schematic diagram of the transceiver of the present embodiment of the invention. In this diagram, $L_1$ and $L_2$ are the inductances of the turns on coil layers 11 and 12 respectively. These coils are magnetically coupled with a coupling coefficient $k_0$, typically higher than 0.85. The effective inductance of the $L_1$ and $L_2$, in series, is shown in equation (1):

$$L = L_1 + L_2 + 2k_0\sqrt{L_1 L_2} \quad (1)$$

The coil of the present embodiment, shown in FIGS. 1 and 2, for example, has:

$$L_1 = L_2 = 4 \text{ µH}$$

and $$k_0 = 0.87.$$

The effective total inductance is therefore equal to 14.8 µH.

The circuit uses three capacitors, two of which are fixed, while the third is a variable tuning capacitor. The variable capacitor range is about 5% of the total capacitance and is used for fine-tuning. The two fixed capacitors are high stability 1% capacitors. The combination of the three capacitors allows the coil to be precisely tuned to within 0.25% of the desired tuning frequency. The small value of the variable capacitor facilitates fine-tuning without risking large shift in the tuning frequency in case of mechanical vibration and stresses.

The shield layers will also have distributed capacitance to $L_1$ and $L_2$, which are not shown in FIG. 4.

Figure 5:
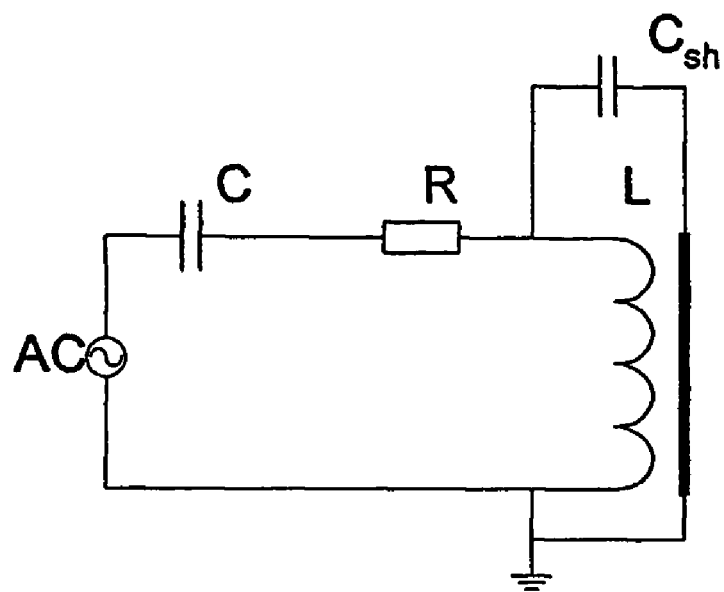
FIG. 5 is a simplified equivalent circuit of the transceiver of FIG. 1.

To study the effect of the shield on the sensitivity of transceiver tuning to stray capacitance, we use the simplified equivalent circuit of FIG. 5. In this circuit, the tuned coil is represented by the series L, R and C. The shield-to-coil capacitance is represented by the capacitance $C_{sh}$.

When the coil is placed away from conductive objects, the resonant frequency of the circuit can be expressed as:

$$f_0 = \frac{1}{2\pi\sqrt{L(C + C_{sh})}} \quad (2)$$

Figure 6:
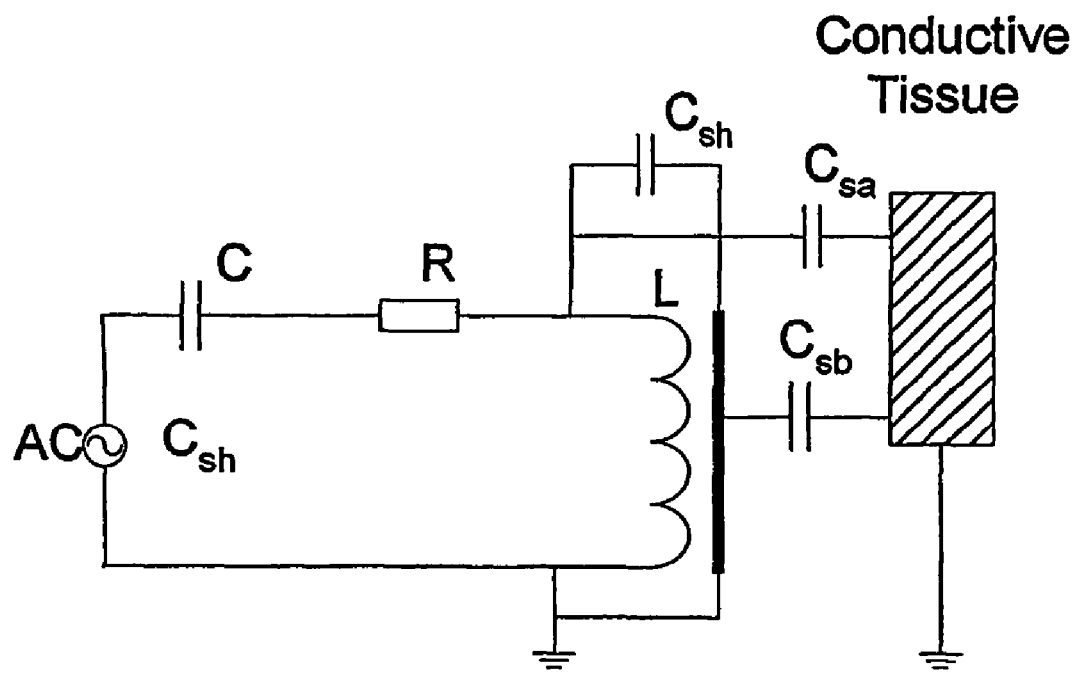
FIG. 6 is an equivalent circuit for calculating the effects of stray capacitance from tissue on the circuit of FIG. 5.
Figure 9A:
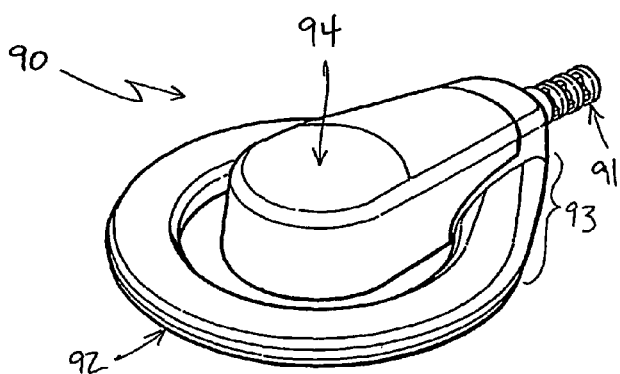
FIG. 9a is a perspective view of an antenna for subcutaneous communication.
Figure 9B:
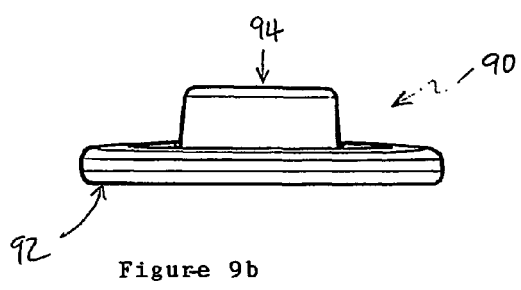
Figure 9C:
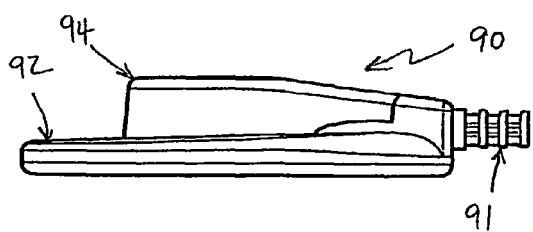
FIG. 9c is a right side view of the antenna of FIGS. 9a and 9b.
Figure 9D:
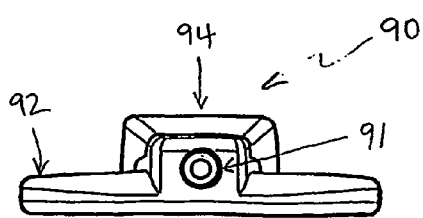
FIG. 9d is a rear view of the antenna of FIGS. 9a to 9c.
Figure 9E:
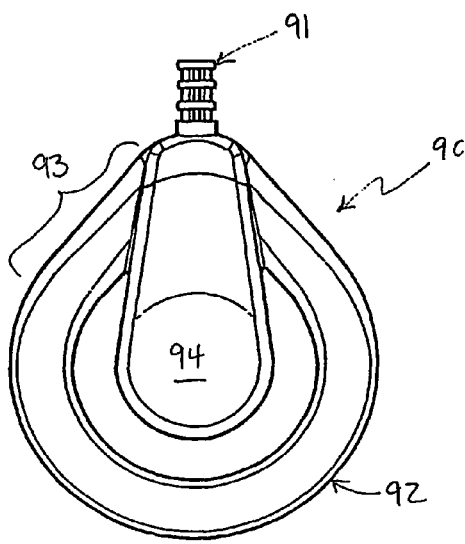
FIG. 9e is a plan view of the antenna of FIGS. 9a to 9d.
Figure 9F:
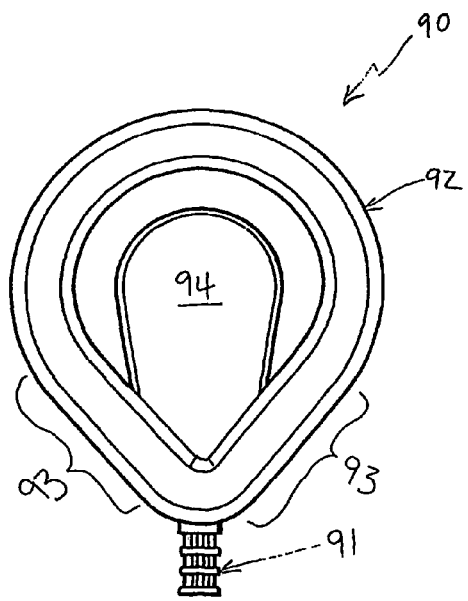
FIG. 9f is an inverted plan view of the antenna of FIGS. 9a to 9e.

FIG. 6 illustrates an equivalent circuit for calculating the effects of stray capacitance from tissue on the circuit of FIG. 5. When the coil is placed close to low conductivity objects, such as human tissue, the main effect will be that of the stray capacitance from the object to the coil. Because the material is assumed to be of low conductivity, compared to metals, the magnetic effects, such as eddy currents, can be ignored. The stray capacitance from the object will be mainly to the shield layer situated between the low conductivity object and the coil, the shield layer being connected to ground. This capacitance is indicated as $C_{sb}$ in FIG. 6. Because the shield layer does not totally enclose the electric field of the inductor, the electric field leakage, linked to the external object, will result in a small capacitance from the external object to the inductor, indicated as $C_{sa}$ in FIG. 6. This capacitance, however, will be much smaller than the capacitance $C_{sb}$ from the object to the shield. The tuned frequency of the coil will then be reduced to:

$$f_1 = \frac{1}{2\pi\sqrt{L(C + C_{sh} + C_{sa})}} \quad (3)$$

The percentage change in the tuned frequency, calculated from the above, is given by:

$$\frac{\Delta f}{f} = \frac{f_1 - f_0}{f_0} = \sqrt{\frac{C + C_{sh}}{C + C_{sh} + C_{sa}}} - 1 \quad (4)$$

To estimate the frequency shift for the above coil when tuned to 4.8 MHz, the tuning capacitance will have a total value of about 50 pF.

$$C + C_{sh} = 50 \text{ pF}$$

When the coil is placed on the skin of the patient, the stray capacitance from the skin to the shield would be in the order of a few picofarads. The capacitance from the skin to the actual inductor is normally less than 0.5 pF, which lowers the tuned frequency by less than 0.5%. The actual value of the stray capacitance depends on factors such as the contact area and the pressure applied to the coil to hold it in place.

In the case of unshielded coils, the stray capacitance from the tissue to the transmitter coil can be high enough to lower the tuned frequency by 2 to 5%, and so it can be seen that the present invention significantly improves the tuning stability of a transceiver.

Although the electrostatic shield reduces the frequency shift caused by stray capacitance to low conductivity objects in the proximity of the transceiver, it has little or no effect on the magnetic coupling to highly conductive materials such as metallic objects.

When the shielded coil is coupled to metallic objects, the eddy currents in that object will generate an opposing magnetic field, which reduces the magnetic field linked to the transmitter coil area. The result is a reduction in the effective inductance of the coil and an increase in the system losses, i.e. a drop in the quality factor. This is similar to the case of unshielded coils.

The temperature sensitivity of the tuned frequency is an important parameter in the design of transcutaneous tuned circuits used in medical applications. In the case of cochlear implants, for example, the patients would wear their speech processors and transmitter coils almost all the time. The coil performance must be stable at all environmental conditions and temperatures to allow patients to use their cochlear implant systems wherever they go and at all possible weather conditions.

The present multi-layer PCB coil embodiment of the invention, described above, can be shown to be less sensitive to temperature variations than a single layer coil.

Equation (1) gives the effective inductance when the coils $L_1$ and $L_2$ are connected in series. Because $L_1$ and $L_2$ are substantially equal, equation (1) can be simplified to:

$$L = 2L_1(1 + k_0) \quad (5)$$

When the temperature increases, the coil expands, leading to an increase in the inductances $L_1$ and $L_2$. In the meantime, the thickness of the PCB material between the coils $L_1$ and $L_2$ will also increase leading to a reduction in the coupling coefficient $k_0$, which partly compensates for the increase in inductance. This can be expressed mathematically by differentiating equation (5):

$$\frac{\partial L}{L} = \left( \frac{1}{L_1} \frac{\partial L_1}{\partial T} + \frac{1}{1 + k_0} \frac{\partial k_0}{\partial T} \right) \Delta T \quad (6)$$

where T is the temperature.

In equation (6), the change in $L_1$ and $k_0$ are of opposite polarities. By the proper choice of the PCB material and layer thicknesses, for a given coil diameter, the temperature sensitivity of the coil, and hence the temperature sensitivity of the tuned frequency, can be minimised.

In medical applications, such as cochlear implants, it is essential to minimise the electromagnetic radiation of transcutaneous transmitter coils. This is important for a number of reasons. Firstly, auditory prosthesis recipients will often be in clinical and hospital environments where electromagnetic radiation can interfere with sensitive electronic equipment. Secondly, some auditory prosthesis recipients, especially school children, may need to use wireless FM systems to listen to a teacher or a speaker. Emission from the cochlear implant transmitter coil can interfere with such systems and render them ineffective and/or useless.

In FIG. 4, the coil terminals are driven from the complementary (antiphase) voltage sources $V_1$ and $V_2$. The tuning capacitors $C_1$, $C_2$ and $C_3$ are connected between the two coils $L_1$ and $L_2$ to achieve a balanced design. This balanced design has the advantage of reduced electromagnetic emission. This is in addition to the reduction in electromagnetic emission due to the electrostatic shield. The end result is a coil with a low level of emission that enables use of the coil close to sensitive electronic devices, such as wireless FM listening receivers, without causing interference problems.

The electromagnetic radiation is one of the strongest considerations in the design of the present embodiment of the invention. The use of an electrostatic shield and a balanced circuit design help reduce electromagnetic emissions and allow use of the transmitter coil in closer proximity to sensitive electronic and communication equipment than is the case for previous coils.

A number of tests were carried out on coil samples to verify the design advantages discussed above. These tests were concerned with stray capacitance effects, temperature stability and electromagnetic emissions.

The first test related to the effects of stray capacitance on coil tuning. In this test, the coil was tuned to 4.8 MHz+/−50 kHz. The coil tuned-frequency was measured while the coil was placed at least 10 cm from conductive objects. The frequency was then measured again while the coil was placed on, and slightly pressed against, the skin of the hand of the operator. The percentage drop in frequency was then calculated. The test was repeated for a second coil with the shield tracks removed.

This test was not a controlled test and the results are not highly accurate. However, the results serve to highlight the advantages of the shield layers. The results are given in the following table:

| Coil type | Free air tuning frequency | Tuning frequency when pressed against skin | Percentage drop in frequency |
|---|---|---|---|
| Shielded | 4.798 MHz | 4.783 MHz | 0.312% |
| Un-shielded | 4.805 MHz | 4.72 MHz | 1.77% |

The results clearly show that the shielded coil is significantly less sensitive to stray capacitance variation.

The second test related to the change of tuned frequency with temperature. In this test, three coil samples were tested. The coils were tuned to 4.7 MHz+/−100 kHz at room temperature. The temperature was then varied and the tuned frequency was measured at different temperatures. The results are given in the following table:

| Coil | Low temp | Room temp | High temp |
| --- | --- | --- | --- |
| Coil 1 | 4.64 MHz @ 6° C. | 4.64 MHz @ 23° C. | 4.649 MHz @ 52.5° C. |
| Coil 2 | 4.6339 MHz @ 5.8° C. | 4.6355 MHz @ 24.4° C. | 4.6376 MHz @ 52.5° C. |
| Coil 3 | 4.7207 MHz @ 4.7° C. | 4.7166 MHz @ 25.2° C. | 4.7213 MHz @ 53.5° C. |

The results show that the change in the tuning frequency of the temperature range of around 5° C. to about 50° C. was within the resolution of the frequency measurements. Coil 1 was the worst of the three coils with a temperature coefficient of 193.5 Hz/° C.

The third test related to electromagnetic emission of coils as described. Coil samples were tested to IEC601-1 standards and passed all tests.

An additional test was carried out, in which a Phonak™ MicroLink FM listening receiver was directly attached to an ESPrit 3G speech processor as produced by Cochlear Ltd. The shielded coil was used in this test to drive a CI24R implant, also as produced by Cochlear Ltd.

Figure 7:
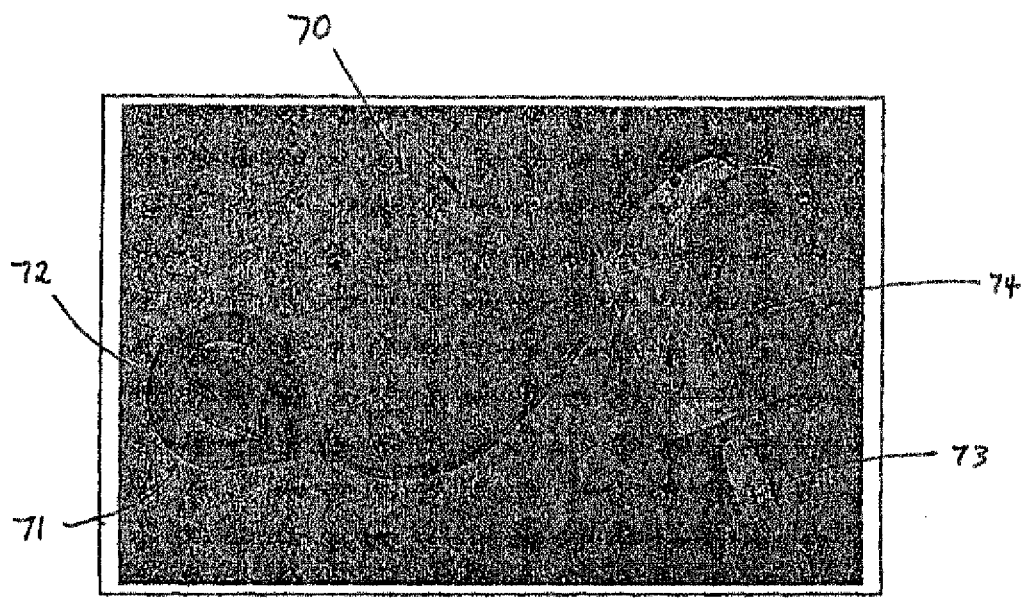
FIG. 7 illustrates an external processing unit with shielded coil and attached FM receiving unit.

The test set-up is shown in FIG. 7, where 70 is the external processing unit including a shielded coil 71 in accordance with the present invention. Coil 71 is of slightly distorted circular shape, with a magnet 72 at the hub of the coil. The MicroLink FM listening receiver 73 is attached directly to the ESPrit 3G speech processor 74, and only about 10 cm from the coil 71.

A Phonak wireless transmitter was placed about 5 metres away inside an acoustic chamber. A loudspeaker was placed in the same chamber and was used to produce a 1 kHz test tone.

Figure 8:
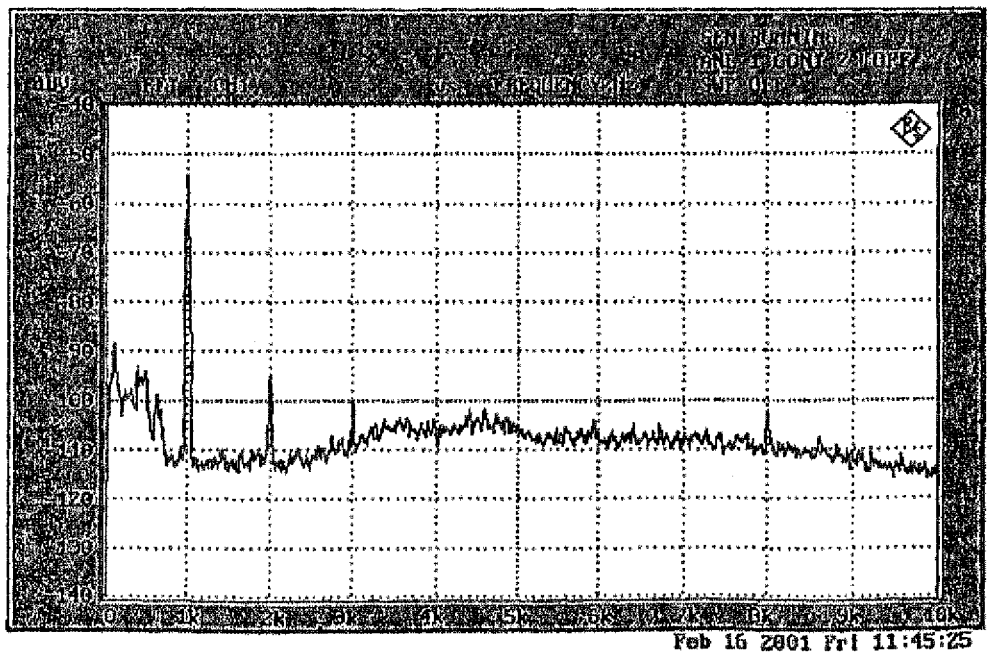
FIG. 8 illustrates the frequency spectrum output of the unit of FIG. 7.

The output signal of the FM MicroLink receiver was monitored to measure the signal to noise ratio. The signal was the received test tone, while the noise was due to the interference from the transmitter circuit of the ESPrit 3G and the shielded transmitter coil 71. FIG. 8 illustrates the measured signals, with a signal to noise ratio of around 35 dB, clearly demonstrating the low emission levels of the shielded coil 71. An unshielded coil will normally interfere with such FM listening systems if they are placed less than perhaps one metre from the speech processor 74 and the coil 71. As can be seen, the present invention allows the FM receiver 73 to become part of an ear-mounted external processing unit 70, being situated perhaps 10 cm from the transmission coil without undue interference.

A new design for transmitter coils used in transcutaneous communication of medical devices has been described. The design is of a tuned transmitter coil with an electrostatic shield implemented using a standard printed circuit board technology. The shielded coil design allows the use of large inductance values and small tuning capacitance values to improve the efficiency of transmission. The electrostatic shields reduce the sensitivity of the tuned frequency to stray capacitance and also reduce the electromagnetic emission of the coil.

FIGS. 9a to 9f illustrate an antenna for subcutaneous communication in accordance with the present invention. The antenna casing 90 comprises a cable inlet 91 for accommodating a cable connection to a coil housed in the casing 90. An outer portion 92 of the casing houses the coil. Distal from the cable inlet 91 the outer portion 92 defines a substantially semicircular annulus following a nominal circumference of a nominal circle. The cable inlet 91 is positioned outside the nominal circumference. Proximal to the cable inlet 91, in regions 93, the outer portion 92 extends substantially tangentially to the nominal circumference towards the cable inlet 91.

The casing 90 further comprises an inner portion 94 for housing a magnet. The inner portion 94 is connected to the outer portion 92 proximal to the cable inlet 91, and the inner portion 94 extends inside the nominal circle formed by the outer portion 92 so as to position the magnet substantially at a centre of the nominal circle.

The inner portion 94 is integrally formed with the outer portion 92, and the casing 90 is formed of plastic. Distal from the cable inlet, the outer portion 92 is a substantially rectangular cross-section annulus, so as to accommodate a coil which is formed on a printed circuit board. Such embodiments of the fifth aspect of the invention may be advantageous in that only a single "spoke", namely, the inner portion 94, is provided in supporting a magnet, thus reducing materials and weight required in forming the antenna casing 90 as compared to the required materials and weight of a "hub and spoke" antenna design. The illustrated embodiment of the invention also provides a stylised attractive antenna, which can be an important consideration where the antenna is to be worn by a user in a prominent body position, such as on the head behind the ear.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A tuned transmitter coil device for transcutaneous RF transmission of power and information from an external component of an auditory prosthesis to an implanted receiver, the transmitter coil device comprising a first shield for reducing a skin-to-coil capacitance, wherein the transmitter coil device and the first shield are formed on a printed circuit board and wherein the transmitter coil device comprises first and second layers of the printed circuit board, each of the first and second layers comprising a respective track, each track, the respective tracks being electrically connected to each other on the printed circuit board and each track defining a spiral with a plurality of turns, the first shield being positioned relative to the first and second layers of the transmitter coil device such that, when the transmitter coil device is brought close to the user's skin for transcutaneous transmission of power and information, the first shield is positioned between the transmitter coil device and the user's skin.

2. The tuned transmitter coil device of claim 1 wherein the first shield is integrally formed with the tuned transmitter coil device.

3. The tuned transmitter coil device of claim 1 wherein each respective spiral defined by the tracks of the first and second layers is substantially circular.

4. The tuned transmitter coil device of claim 1 wherein the dimensions of the track of each of the first and second layers are predetermined in order to control electrical performance of the transmitter coil device.

5. The tuned transmitter coil device of claim 4 wherein the number of turns of each of the spirals is predetermined in order to control electrical performance of the transmitter coil device.

6. The tuned transmitter coil device of claim 4 wherein the radial spacing between adjacent turns of the spiral is predetermined in order to control electrical performance of the transmitter coil device.

7. The tuned transmitter coil device of claim 4 wherein a substrate of the printed circuit board is selected in order to control electrical performance of the transmitter coil device.

8. The tuned transmitter coil device of claim 1 wherein each turn of the spiral of the first layer is placed adjacent to a respective gap between turns of the spiral of the second layer.

9. The tuned transmitter coil device of claim 1 wherein the first shield is formed on a third layer of the printed circuit board integrally formed with the first and second layers of the printed circuit board.

10. The tuned transmitter coil device according to claim 9 wherein the first shield is defined by tracks on the third layer, extending in a region adjacent to the spirals of the first and second layers.

11. The tuned transmitter coil device according to claim 10 wherein the tracks defining the first shield are in the form of a plurality of substantially concentric open loops, and wherein each of the open loops are electrically grounded.

12. The tuned transmitter coil device of claim 11 wherein the tracks defining the open loops of the first shield have a small width relative to a width of the tracks of the first and second layers.

13. The tuned transmitter coil device of claim 11 wherein each open loop of the first shield is positioned adjacent to a gap between turns of the spiral of the adjacent layer.

14. The tuned transmitter coil device according to claim 9 further comprising a second shield for reducing electromagnetic emissions from the transmitter coil device.

15. The tuned transmitter coil device according to claim 14 wherein the second shield is placed on a side of the transmitter coil device opposite to a side of the transmitter coil device on which the first shield is placed.

16. The tuned transmitter coil device according to claim 14 wherein the second shield extends in a region substantially adjacent to the spirals of the first and second layers.

17. The tuned transmitter coil device of claim 14 wherein the transmitter coil device and the first shield are formed on the printed circuit board, and wherein the second shield is defined by tracks on a fourth layer of the printed circuit board.

18. The tuned transmitter coil device according to claim 17, wherein the tracks defining the second shield extend substantially within a region adjacent to the turns of the spirals of the first and second layers.

19. The tuned transmitter coil device according to claim 17 wherein the tracks defining the second shield are in the form of a plurality of substantially concentric open loops.

20. The tuned transmitter coil device of claim 19 wherein each of the open loops are electrically grounded.

21. The tuned transmitter coil device of claim 17 wherein the tracks defining the second shield have a small width relative to a width of the tracks of the first and second layers.

22. The tuned transmitter coil device of claim 17 wherein the tracks defining the second shield are positioned adjacent to gaps between turns of the spiral of an adjacent layer of the printed circuit board.

23. A transceiver for an auditory prosthesis comprising:
a tuned transmitter coil for transcutaneous transmissions, tuned to a desired frequency of transmission; and
a first shield for reducing a skin-to-coil capacitance wherein the transmitter coil and the first shield are formed on a printed circuit board and wherein the transmitter coil comprises first and second layers of the printed circuit board, each of the first and second layers comprising a respective track, the respective tracks being electrically connected to each other on the printed circuit board and each track defining a spiral with a plurality of turns, the first shield being positioned relative to the transmitter coil such that, when the transmitter coil is brought close to a user's skin for transcutaneous transmission of power and information, the first shield is positioned between the transmitter coil and the user's skin.

24. The transceiver of claim 23 wherein the first shield is integrally formed with the tuned transmitter coil.

25. The transceiver of claim 23 wherein each respective spiral defined by the tracks of the first and second layers is substantially circular.

26. The transceiver of claim 23 wherein the dimensions of the track of each of the first and second layers are predetermined in order to control electrical performance of the coil.

27. The transceiver of claim 26 wherein the number of turns of each of the spirals is predetermined in order to control electrical performance of the coil.

28. The transceiver of claim 26 wherein the radial spacing between adjacent turns of the spiral is predetermined in order to control electrical performance of the coil.

29. The transceiver of claim 26 wherein a substrate of the printed circuit board is selected in order to control electrical performance of the coil.

30. The transceiver of claim 23 wherein each turn of the spiral of the first layer is placed adjacent to a respective gap between turns of the spiral of the second layer.

31. The transceiver of claim 23 wherein the first shield is formed on a third layer of the printed circuit board integrally formed with the first and second layers of the printed circuit board.

32. The transceiver according to claim 31 wherein the first shield is defined by tracks on the third layer, extending in a region adjacent to the spirals of the first and second layers.

33. The transceiver according to claim 32 wherein the tracks defining the first shield are in the form of a plurality of substantially concentric open loops, and wherein each of the open loops are electrically grounded.

34. The transceiver of claim 33 wherein the tracks defining the open loops of the first shield have a small width relative to a width of the tracks of the first and second layers.

35. The transceiver of claim 33 wherein each open loop of the first shield is positioned adjacent to a gap between turns of the spiral of the adjacent layer.

36. The transceiver of claim 23 further comprising a second shield for reducing electromagnetic emissions from the transmitter coil.

37. The transceiver according to claim 36 wherein the second shield is placed on a side of the transmitter coil opposite to a side of the transmitter coil on which the first shield is placed.

38. The transceiver according to claim 36 wherein the second shield extends in a region substantially adjacent to the spirals of the first and second layers.

39. The transceiver of claim 36, wherein the coil and the first shield are formed on the printed circuit board, and wherein the second shield is defined by tracks on a fourth layer of the printed circuit board.

40. The transceiver according to claim 39, wherein the tracks defining the second shield extend substantially within a region adjacent to the turns of the spirals of the first and second layers.

41. The transceiver according to claim 39 wherein the tracks defining the second shield are in the form of a plurality of substantially concentric open loops.

42. The transceiver of claim 41 wherein each of the open loops are electrically grounded.

43. The transceiver of claim 39 wherein the tracks defining the second shield have a small width relative to a width of the tracks of the first and second layers.

44. The transceiver of claim 39 wherein the tracks defining the second shield are positioned adjacent to gaps between turns of the spiral of an adjacent layer of the printed circuit board.

45. An external processor unit for an auditory prosthesis, comprising:
   a transceiver comprising a tuned transmitter coil for transcutaneous transmission, tuned to a desired frequency of transmission; and
   a first shield for reducing a skin-to-coil capacitance wherein the transmitter coil and the first shield are formed on a printed circuit board and wherein the transmitter coil comprises first and second layers of the printed circuit board, each of the first and second layers comprising a respective track, the respective tracks being electrically connected to each other on the printed circuit board and each track defining a spiral with a plurality of turns the first shield being positioned relative to the transmitter coil such that, when the transmitter coil is brought close to a user's skin for transcutaneous transmission of power and information, the first shield is positioned between the transmitter coil and the user's skin.

46. The external processor unit of claim 45 wherein the first shield is integrally formed with the tuned transmitter coil.

47. The external processor unit of claim 45 wherein each respective spiral defined by the tracks of the first and second layers is substantially circular.

48. The external processor unit of claim 45 wherein the dimensions of the track of each of the first and second layers are predetermined in order to control electrical performance of the coil.

49. The external processor unit of claim 48 wherein the number of turns of each of the spirals is predetermined in order to control electrical performance of the coil.

50. The external processor unit of claim 48 wherein the radial spacing between adjacent turns of the spiral is predetermined in order to control electrical performance of the coil.

51. The external processor unit of claim 48 wherein a substrate of the printed circuit board is selected in order to control electrical performance of the coil.

52. The external processor unit of claim 45 wherein each turn of the spiral of the first layer is placed adjacent to a respective gap between turns of the spiral of the second layer.

53. The external processor unit claim 45 wherein the first shield is formed on a third layer of the printed circuit board integrally formed with the first and second layers of the printed circuit board.

54. The external processor unit according to claim 53 wherein the first shield is defined by tracks on the third layer, extending in a region adjacent to the spirals of the first and second layers.

55. The external processor unit according to claim 54 wherein the tracks defining the first shield are in the form of a plurality of substantially concentric open loops, and wherein each of the open loops are electrically grounded.

56. The external processor unit of claim 55 wherein the tracks defining the open loops of the first shield have a small width relative to a width of the tracks of the first and second layers.

57. The external processor unit of claim 55 wherein each open loop of the first shield is positioned adjacent to a gap between turns of the spiral of the adjacent layer.

58. The external processor unit of claim 45 further comprising a second shield for reducing electromagnetic emissions from the transmitter coil.

59. The external processor unit according to claim 58 wherein the second shield is placed on a side of the transmitter coil opposite to a side of the coil on which the first shield is placed.

60. The external processor unit according to claim 58 wherein the second shield extends in a region substantially adjacent to the spirals of the first and second layers.

61. The external processor unit of claim 58, wherein the coil and the first shield are formed on the printed circuit board, and wherein the second shield is defined by tracks on a fourth layer of the printed circuit board.

62. The external processor unit according to claim 61, wherein the tracks defining the second shield extend substantially within a region adjacent of the spirals of the first and second layers.

63. The external processor unit according to claim 61 wherein the tracks defining the second shield are in the form of a plurality of substantially concentric open loops.

64. The external processor unit of claim 63 wherein each of the open loops are electrically grounded.

65. The external processor unit of claim 61 wherein the tracks defining the second shield have a small width relative to a width of the tracks of the first and second layers.

66. The external processor unit of claim 61 wherein the tracks defining the second shield are positioned adjacent to gaps between turns of the spiral of an adjacent layer of the printed circuit board.

67. An external processor unit for an auditory prosthesis, comprising:
   a transmitter coil for transmission of transcutaneous electromagnetic signals to an implant;
   a receiver for receiving wireless transmissions from a signal source; and
   a shield for reducing electromagnetic emissions of the transmission coil wherein the transmitter coil and the shield are formed on a printed circuit board and wherein the transmitter coil comprises first and second layers of the printed circuit board, each of the first and second layers comprising a respective track, the respective tracks being electrically connected to each other on the printed circuit board and each track defining a spiral with a plurality of turns, the shield being placed relative to the transmitter coil such that when the transmitter coil is brought into proximity to the user's skin for transcutaneous transmission, the shield is positioned between the transmitter coil and the user's skin.

68. The external processor unit of claim 67 wherein each respective spiral defined by the tracks of the first and second layers is substantially circular.

69. The external processor unit of claim 67 wherein the dimensions of the track of each of the first and second layers are predetermined in order to control electrical performance of the coil.

70. The external processor unit of claim 69 wherein the number of turns of each of the spirals is predetermined in order to control electrical performance of the coil.

71. The external processor unit of claim 69 wherein the radial spacing between adjacent turns of the spiral is predetermined in order to control electrical performance of the coil.

72. The external processor unit of claim 69 wherein a substrate of the printed circuit board is selected in order to control electrical performance of the coil.

73. The external processor unit of claim 69 wherein each turn of the spiral of the first layer is placed adjacent to a respective gap between turns of the spiral of the second layer.

74. The external processor unit of claim 67 wherein the shield extends in a region substantially adjacent to the spirals of the first and second layers.

75. The external processor unit of claim 67, wherein the shield is defined by tracks on a fourth layer of the printed circuit board.

76. The external processor unit according to claim 75, wherein the tracks defining the shield extend substantially within a region adjacent to the turns of the spirals of the first and second layers.

77. The external processor unit according to claim 75 wherein the tracks defining the shield are in the form of a plurality of substantially concentric open loops.

78. The external processor unit of claim 77 wherein each of the open loops are electrically grounded.

79. The external processor unit of claim 75 wherein the tracks defining the shield have a small width relative to a width of the tracks of the first and second layers.

80. The external processor unit of claim 75 wherein the tracks defining the shield are positioned adjacent to gaps between turns of the spiral of an adjacent layer of the printed circuit board.

81. The external processor unit of claim 67 wherein the external processor unit is adapted for mounting on a user's ear.

82. The external processor unit of claim 67 wherein the external processor unit comprises a cable to the transmission coil to allow the transmission coil to be placed behind a user's ear, for coupling with an implant.

* * * * *

UNITED STATES PATENT AND TRADEMARK OFFICE
CERTIFICATE OF CORRECTION

PATENT NO. : 7,260,435 B2
APPLICATION NO. : 10/250831
DATED : August 21, 2007
INVENTOR(S) : Ibrahim It is certified that error appears in the above-identified patent and that said Letters Patent is hereby corrected as shown below:

In the Drawings

| | |
|---|---|
| FIG. 8, Sheet 6 of 7 | Delete Drawing Sheet 6 and substitute therefore the Drawing Sheet, consisting of Figs. 7 & 8, as shown on the attached page |
| Column 12, line 44, Claim 1 | Delete "each track," |
| Column 15, line 26, Claim 45 | Delete "turns the", Insert --turns, the-- |
| Column 15, line 56, Claim 53 | After "unit", Insert --of-- |
| Column 16, line 24, Claim 62 | After "adjacent", Insert --to the turns-- |

Signed and Sealed this

Twenty-ninth Day of September, 2009

David J. Kappos
*Director of the United States Patent and Trademark Office*